United States Patent

Brace et al.

[11] Patent Number: 4,726,225
[45] Date of Patent: Feb. 23, 1988

[54] SURFACE ACOUSTIC WAVE GAS FLOW RATE SENSOR WITH SELF-HEATING FEATURE

[75] Inventors: John G. Brace, Brown Deer; Thomas S. Sanfelippo, Shorewood, both of Wis.

[73] Assignee: Johnson Service Company, Milwaukee, Wis.

[21] Appl. No.: 899,439

[22] Filed: Aug. 22, 1986

[51] Int. Cl.$^4$ .................................................. G01F 1/68
[52] U.S. Cl. ................................... 73/204; 310/313 R; 310/313 D; 73/DIG. 4
[58] Field of Search ........................... 73/204, DIG. 4; 310/313 R, 313 B, 313 C, 313 D; 333/155; 375/117, 119

[56] References Cited

U.S. PATENT DOCUMENTS 3,983,424  9/1976  Parhs ..................................... 333/155
4,332,157  6/1982  Zemel et al. ........................... 73/204

OTHER PUBLICATIONS

Ahmad, "Surface Acoustic Wave Sensor" in IEEE Ultrasonics Symposium, 10/85.

Primary Examiner—Herbert Goldstein
Attorney, Agent, or Firm—Larry L. Shupe; Alexander M. Gerasimow

[57] ABSTRACT

A surface acoustic wave device for measuring the mass flow rate of a gas includes a surface acoustic wave delay line formed of a piezoelectric substrate and having a temperature coefficient of delay on the order of $10^{-4}/°C$. The substrate has disposed thereon a transmitting and a receiving interdigital transducer, the transducers being configured to have an operating frequency in the range of from 10MHz to 1000MHz. That portion of the substrate located between the transducers defines a propagation region and has a medium deposited thereon for absorbing a portion of the acoustical and/or electrical energy flowing thereacross. This absorbed energy increases the temperature of the propagation region over that of the surrounding ambient.

A mass flow of the gas across the sensor will decrease its temperature and result in an upward shift in the resonant frequency. A suitable amplifier and resonant frequency detector may be coupled to the sensor for detecting the change in resonant frequency, thereby permitting mass flow rate measurement.

9 Claims, 5 Drawing Figures

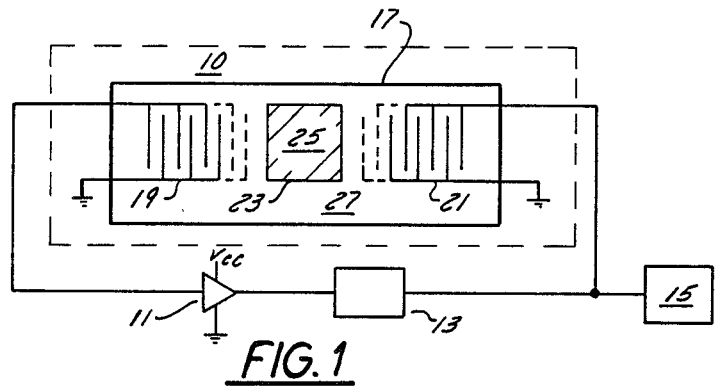
FIG. 1
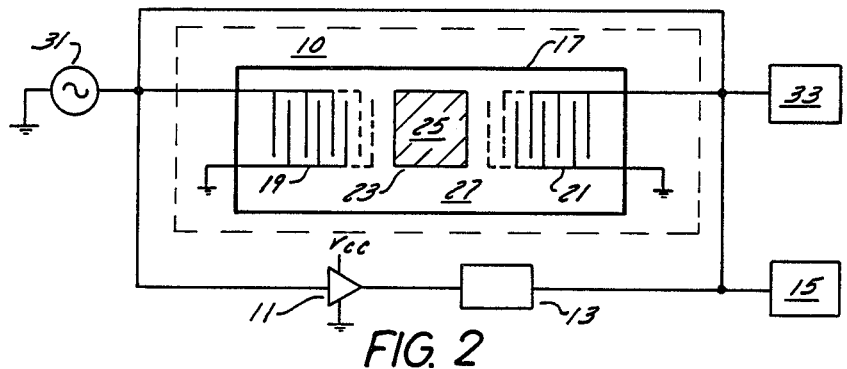
FIG. 2
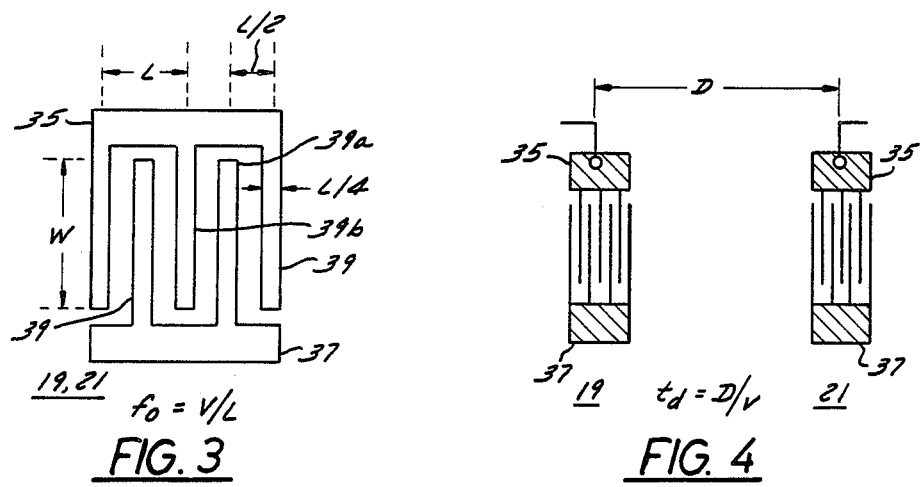
FIG. 3
FIG. 4

SURFACE ACOUSTIC WAVE GAS FLOW RATE SENSOR WITH SELF-HEATING FEATURE

This invention relates generally to sensors and, more particularly, to a surface acoustic wave gas flow rate sensor with a self-heating capability.

Gas flow rate sensors are widely used for detecting the mass flow rate of a gas through a confined duct. Merely by way of example, one application for such sensors is in process controls, an aspect of which includes the control of heating, ventilating and air conditioning (HVAC) control systems where it is often desirable to continuously monitor and control the rate of flow of air through a particular duct.

One known approach to the detection and transduction of the mass flow rate of a gas involves the use of a plurality of temperature coefficient thermistors disposed in a regular, spaced-apart relationship within a duct and in an orientation to define a plane which is normal to the axis of flow of the gas. Support is typically by a lattice of wires supported horizontally and vertically across the passage to define a grid. With a known voltage applied to each thermistor having a known temperature coefficient characteristic, the resulting temperature rise over that of surrounding quiescent gas is also known. So long as the temperature of the gas flowing across the thermistors is different from that of the thermistors themselves, the mass flow rate may be determined by detecting the change in thermistor temperature, as evidenced by changes in thermistor current or voltage, from that which existed in the quiescent state.

Another approach to the detection and transduction of the mass flow rate of gases is shown and described in a paper titled "Surface Acoustic Wave Flow Sensor" authored by Nisar Ahmad and presented at the IEEE Ultrasonics Symposium on Oct. 17, 1985. The apparatus described therein comprises a surface acoustic wave (SAW) flow sensor which incorporates a separate resistive element embodied as a thin film heater which operates to raise the temperature of the SAW substrate. The heater is energized by a separate voltage source and a flow of gas thereacross will lower the temperature of the substrate resulting is a detectable change in the frequency of the SAW delay line oscillator. This change in frequency may then be used to compute the mass flow rate.

While these devices have heretofore been generally satisfactory for detecting the mass flow rate of a gas, they have failed to appreciate the manner in which an SAW sensor may be constructed to be self heating solely by the radio frequency (RF) signal which is applied to the delay line, thereby avoiding the necessity of a separate heater strip and related power source.

SUMMARY OF THE INVENTION

In general, a surface acoustic wave device for measuring the mass flow rate of a gas includes a surface acoustic wave delay line formed of a piezoelectric substrate and having a temperature coefficient of delay on the order of $10^{-4}/°$ C. The substrate has disposed thereon a transmitting and a receiving interdigital transducer, the transducers being configured to have an operating frequency in the range of from 10 MHz to 1000 MHz. That portion of the substrate surface located between the transducers defines a propagation region and has a medium deposited thereon for absorbing a portion of the acoustical and/or electrical energy flowing thereacross. This absorbed energy increases the temperature of the propagation region over that of the surrounding ambient.

A mass flow of the gas across the sensor will decrease its temperature and result in an upward shift in the resonant frequency. A suitable amplifier and resonant frequency detector may be coupled to the sensor for detecting the change in resonant frequency, thereby permitting mass flow rate measurement.

It is an object of the invention to provide an SAW device for measuring the mass flow rate of a gas.

Another object of the invention is to provide an SAW device which uses heat transfer characteristics to determine the mass flow rate of a gas.

Still another object of the invention is to provide an SAW device which is self-heating.

Yet another object of the invention is to provide an SAW device wherein its temperature rise is solely a result of the application of an RF signal thereto. How these and other objects are accomplished will become more apparent from the following detailed description thereof taken in conjunction with the drawing.

DESCRIPTION OF THE DRAWING

FIG. 1 is a simplified top plan view of the inventive self-heating sensor shown in conjunction with associated electrical devices and which uses resonant frequency techniques for determining mass flow rate;

FIG. 2 is a simplified top plan view of the sensor of FIG. 1 shown in conjunction with other associated electrical devices for determining mass flow rate using phase shift techniques;

FIG. 3 is a simplified top plan view, greatly enlarged, of one of the interdigital transducers of the sensor of FIG. 1., FIG. 4 is a simplified top plan view, greatly enlarged, of the interdigital transducers of the sensor of FIG. 1, and;

DESCRIPTION OF A PREFERRED EMBODIMENT

Figure 5:
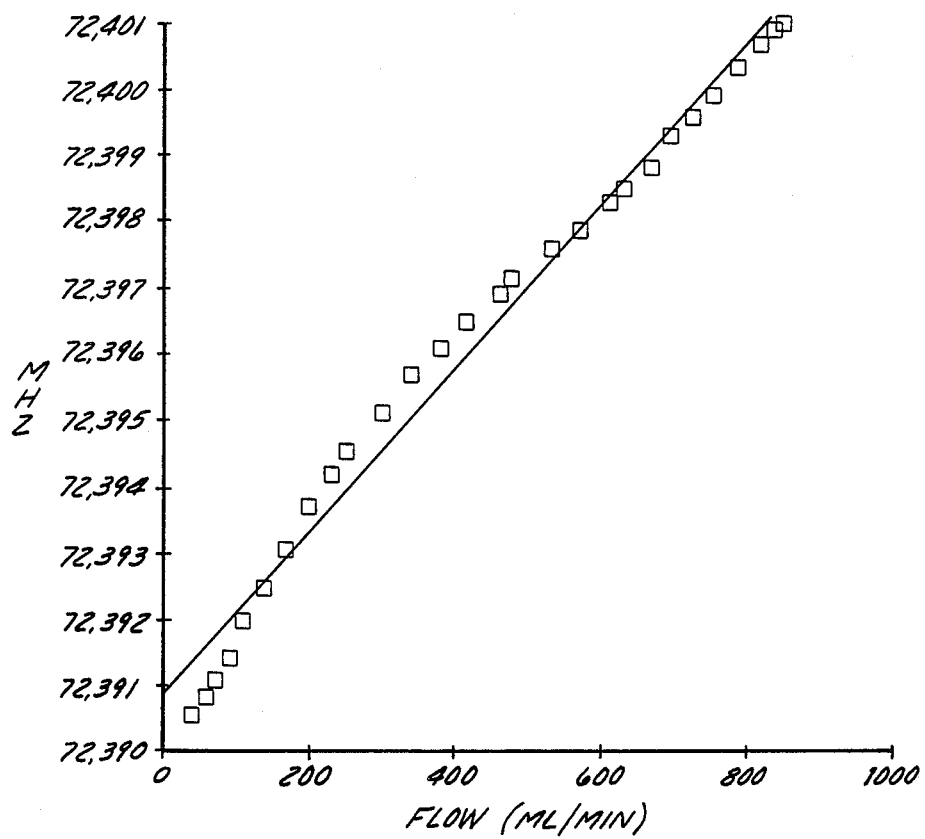
FIG. 5 is a graphical depiction of changes in resonant frequency resulting from changes in mass flow rate.

Referring to FIG. 1, the sensor 10 is shown in conjunction with an RF amplifier 11, an attenuator 13 and a frequency counter 15, the purposes of which will be described hereinafter. The sensor 10 includes a piezoelectric substrate 17 having disposed thereon a first, transmitting interdigital transducer 21 for generating a surface acoustical wave upon the substrate 17 and a second, receiving interdigital transducer 19 for detecting the surface wave and converting it to an RF signal. The material from which the substrate 17 is made, its crystallographic orientation and the geometry and orientation of the transducers 19, 21 can be selected to give a resonant frequency $F_o$, a delay time $T_d$, a temperature coefficient of delay (TCD) or temperature coefficient of frequency (TCF), a frequency bandwidth and an insertion loss that may all be well controlled.

A thin film 23 of an energy absorbing medium is disposed on the substrate 17 in a propagation region 25 intermediate the transducers 19, 21 for coupling energy from the surface of the substrate 17, thereby generating heat. The heat so generated will elevate the temperature of the sensor 10 over that of the surrounding ambient gas in a quiescent state while a mass flow of the gas across the sensor 10 will decrease its temperature and result in a shift in the resonant frequency which is measurable and convertible to mass flow rate.

The substrate 17 may be made of or overlaid with a piezoelectric material selected in accordance with the desired parameters of the application. Set forth below is a tabular listing of the approximate temperature coefficients of a few piezoelectric materials together with their crystallographic orientation.

| TEMPERATURE COEFFICIENTS | |
|---|---|
| MATERIAL | (TCD, PPM/°C.) |
| QUARTZ Y, Z | +24 |
| LiTaO$_3$ Y, Z | −35 |
| LiNbO$_3$ Y, Z | −94 |
| LiNbO$_3$ 128°-Y, X | −90 |

The significance of the algebraic sign and absolute value of these and other temperature coefficients of other piezoelectric materials is that they are indicative of the magnitude and direction of change in $V_a$, propagation velocity as described below, and therefore, of the magnitude and direction of the shift in resonant frequency $F_o$. While an exemplary sensor 10 will be described which has particular characteristics, it is to be appreciated that other sensors may be constructed to have differing characteristics after appreciating the teaching of this specification.

More particularly and referring further to FIGS. 1 and 3, an exemplary substrate 17 was made of 128° rotated Y-cut, X-propagating LiNbO$_3$ and had overall dimensions of approximately 10 mm. in length, 20 mm. in width and 0.5 mm. in thickness. The top surface 27 thereof was highly polished in preparation for the deposition of the transducers 19, 21 and the film 23 thereon and a suitable substrate 17 is commercially available from several suppliers. The transducers 19, 21 may be of any one of a variety of materials including aluminum or nickel and may be formed by vacuum deposition upon the substrate 17 and subsequently etched to the desired geometry using known photolithographic techniques.

Referring next to FIG. 2, the inventive sensor 10 is shown in conjunction with an RF oscillator 31 and a signal detector 33 in addition to the amplifier 11, attenuator 13 and frequency counter 15 illustrated in FIG. 1, the purposes of which will be described hereinafter.

Referring further to FIGS. 1 and 3, each of the transducers 19, 21 is shown to include a first interdigital electrode 35 and a second interdigital electrode 37 and while the view of FIG. 3 has been simplified, each electrode 35, 37 was configured to have fifteen fingers 39. The resonant frequency $F_o$ for each such transducer 19, 21 is represented by the equation $F_o = V_a/L$ where $V_a$ is the velocity in meters per second of the Rayleigh or mechanical wave propagating across the surface 27, $F_o$ is the resonant frequency in Hertz and L is the acoustical wavelength, i.e., the center-to-center distance in meters between any two adjacent fingers 39 on a particular electrode 35 or 37. From FIG. 3, it is apparent that this equation also governs the center-to-center spacing of a finger 39 of the first electrode 35 and either adjacent finger 39 of the second electrode 37, the spacing of fingers 39a and 39b for example, as well as the width of each. Additionally, the number of finger pairs N determines the percentage bandwidth of the sensor 10 as a function of the resonant frequency $F_o$ in accordance with the equation N = 1/percentage bandwidth = $F_o$/delta F.

Referring additionally to FIG. 4, the time delay of propagation $T_d$ is governed by the equation $T_d = D/V_a$ where D is the propagation distance, i.e., the center-to-center distance between transducers 19, 21 in meters, $V_a$ is the acoustical velocity of propagation in meters per second and $T_d$ is in seconds. Given the foregoing equations, one may configure a substrate 17 with transducers 19, 21 to have predictable nominal bandwidth, resonant frequency and delay characteristics. In an exemplary configuration, L was selected to be 52.5 micrometers, the aperture width W was selected to be 3.5 mm, D was selected to be 4.5 mm and N was selected to be 15 electrode pairs which resulted in a sensor 10 having a nominal resonant frequency of 75MHz and a 6dB bandwidth of 4.8 MHz.

Referring again to FIGS. 1 and 2, a suitable thin film 23 may be formed of any material which may exist in solid phase at the ambient temperature of the environment and which is capable of being deposited in the aforementioned propagation region 25 in thicknesses ranging from nominally about 1% to 10% of the acoustical wavelength L. A preferred material will also be capable of absorbing energy from the substrate surface 27, i.e., from the mechanical Rayleigh wave propagating thereacross and/or from the electric field associated with this wave and due to piezoelectric property of the substrate 17, thereby providing self-heating. One example of such a material is nickel-chromium alloy which may be deposited in the propagation region 25 by evaporation or sputtering. In this instance, energy absorption will primarily be due to coupling with the electric field. Another example of a preferred material is a nonconductive polymer such as poly(methylmethacrylate) which will result in energy coupling primarily due to the mechanical wave. Yet other suitable classes of materials would include conductive polymers, cermets and composite microwave absorbers such as iron in a methacrylate or epoxy matrix. Deposition may be by spraying, spincoating, chemical vapor deposition, painting or solution application.

After having made a sensor 10 in accordance with the teachings of this specification, it may be connected in a circuit as generally shown in FIG. 1 which includes the sensor 10, a 50 ohm variable attenuator 13, a broadband amplifier 11 and a signal detector 15 such as a digital frequency counter.

Using the exemplary sensor 10, a DC power of 15 volts at 150 mA was applied to the amplifier 11 and with the attenuator 13 set at 1 dB, the circuit oscillated at about 72.4 MHz with a peak-to-peak amplitude of 1.25 volts. The temperature of the sensor 10 rose from an ambient of 23.8° C. to 24.0° C., the latter being the stabilized elevated temperature. When a mass flow of dry nitrogen was passed over the sensor 10, the oscillation frequency varied by 3 kHz corresponding to a flow variation of between 0 and 690 ml per minute.

In another example, a DC voltage of 20 volts was applied to the amplifier 11 and the attenuator 13 set at 1 dB. The circuit oscillated at about 72.4 MHz with an amplitude of 4 volts peak-to-peak and the sensor temperature rose from an ambient of 23.8° C. to a steady state elevated temperature of 24.6° C. As shown in FIG. 5, the oscillation frequency varied by 10.3 kHz for a mass flow variation ranging from 38 to 846 ml per minute. It will also be appreciated that the change in resonant resulting from the change in flow was substantially linear across the selected flow range.

When the sensor 10 is overdriven as in the second example, it will be noted that a greater frequency variation will result with a given change in mass flow rate of tne gas, thereby simplifying resolution by a digital frequency counter 15. Therefore, very small changes in flow at the surface of the propagation region 25 may be easily resolved, permitting the accurate computation by known methods of the mass flow rate of the gas passing thereacross.

In the circuit configuration of FIG. 2, an RF oscillator 31 or signal generator and a signal detector 33 are additionally employed with the circuit of FIG. 1. The oscillator 31 provides a signal at the nominal resonant frequency of the sensor 10 and the signal detector 33 measures the shift in phase between the signal applied at the first, transmitting interdigital transducer 21 and that received at the second, receiving interdigital transducer 19. The variation in magnitude of this phase shift will likewise permit computation of mass flow rate. Yet another approach to the determination of mass flow rates is by the detection of the time delay and changes therein between the time of application of a signal at the transmitting interdigital transducer 21 and its arrival at the receiving interdigital transducer 19.

While the implementations of FIGS. 1 and 2 are both very sensitive and will yield highly accurate results, that of FIG. 1 is the simpler and is significantly less expensive in its implementation. It is also to be appreciated that changes in resonant frequency as measured using the arrangement of FIG. 1 and changes in phase as measured using that of FIG. 2 are solely due to changes in temperature of the self-heating propagation region 25 which result from changes in the mass flow rate of the gas flowing thereacross.

Using the techniques described above, one may configure a sensor 10 to have a resonant frequency in the range of 10 MHz–1000 MHz, this representing the nominal practical range available using known fabrication techniques although the selection of higher resonant design frequencies will likely be attended by increased difficulties in fabrication of the sensor 10. One factor which may govern the resonant frequency selected is that intrinsic temperature sensitivity, in change in resonant frequency per degree change in the temperature of the surface, increases with increasing resonant frequency. It is also to be appreciated that temperature rise by self-heating of the propagation region 25 is generally governed by the formula delta $T \alpha 1/A$ where A is the area of the propagation region 25; that is, for a given sensor 10 and input power level, the temperature of the region 25 and the sensitivity of the sensor 10 both increase with decreases in A. Additionally, selection of higher design resonant frequencies indicate a decrease in the area A to maintain a given temperature rise.

Similar structures may be used for the determination of mass flow rate using the teaching of the specification, such structures including the use of a piezoelectric polymer to form a propagation region 25 upon a nonpiezoelectric substrate. Another structure could employ a selective thinning of the propagation region 25, thereby permitting the excitation of measurable Lamb waves. One may also use bulk wave crystal oscillators in a self-heating mode or surface acoustical wave resonators.

While only a few preferred embodiments have been shown and described herein, it is not intended to be limited thereby but only by the scope of the claims which follow.

We claim:

1. A surface acoustic wave device for measuring the mass flow rate of a gas and including:
    a surface acoustic wave delay line formed of a piezoelectric material having a temperature coefficient of delay on the order of $10^{-4}/°$ C. and having disposed thereon a transmitting interdigital transducer and a receiving interdigital transducer, said transducers having an operating frequency in the range of from 10 MHz to 1000 MHz;
    a propagation region located intermediate said transducers, said region having a medium deposited thereon for absorbing a portion of the energy associated with the acoustic wave flowing thereacross, thereby heating said region and increasing the temperature of said region over that of the surrounding ambient.

2. The invention set forth in claim 1 wherein said transducers have a resonant frequency of about 75 MHz.

3. The invention set forth in claim 2 wherein said substance deposited on said propagation region is selected to result in an additional insertion loss of from about 5 dB to about 15 dB.

4. A method for measuring the flow rate of a gas in a duct and including the steps of:
    providing a surface wave delay line disposed in said duct and having a transmitting interdigital transducer and a receiving interdigital transducer, a propagation region disposed between said transducers, said region having a medium deposited thereon for absorbing energy trom a propagating surface wave, thereby heating said region and increasing the temperature of said region above that of a surrounding ambient;
    providing an amplifier coupled to said delay line and coacting therewith to define a stabilized oscillator;
    providing a frequency counter coupled to said delay line for determining a resonant frequency of said oscillator, and;
    determining the flow rate of said gas through said duct.

5. The invention set forth in claim 4 wherein the determination step includes the steps of:
    energizing said amplifier;
    measuring a first frequency of said oscillator when said gas is flowing across said region at a first, known rate;
    measuring a second frequency of said oscillator when said gas is flowing across said region at a second, known rate, thereby establishing the change in resonant frequency per unit change in gas flow rate;
    measuring a third frequency of said oscillator when said gas is flowing across said region at a third rate to be determined, and;
    computing said third rate.

6. The invention set forth in claim 5 wherein said delay line is formed on a piezoelectric material having a temperature coefficient of delay greater than $5 \times 10^{-5}/°$ C.

7. The invention set forth in claim 6 wherein said means for increasing the temperature of said region includes a substance disposed on said propagation region for absorbing a portion of the acoustical energy flowing across said region, thereby increasing its temperature above that of the surrounding ambient.

8. The invention set forth in claim 6 wherein said means for increasing the temperature of said region includes a substance disposed on said propagation region for absorbing a portion of the electrical energy flowing across said region, thereby increasing its temperature above that of the surrounding ambient.

9. The invention set forth in claim 6 wherein said means for increasing the temperature of said region includes a substance disposed on said propagation region for absorbing a portion of the acoustical and electrical energy flowing across said region, thereby increasing its temperature above that of the surrounding ambient.

* * * * *